US010491814B2

(12) United States Patent
Tamai et al.

(10) Patent No.: US 10,491,814 B2
(45) Date of Patent: Nov. 26, 2019

(54) IMAGE PROCESSING APPARATUS (71) Applicant: OLYMPUS CORPORATION, Tokyo (JP)

(72) Inventors: Hiroshi Tamai, Tokyo (JP); Tadao Eto, Tokyo (JP); Daisuke Sano, Yokohama (JP)

(73) Assignee: OLYMPUS CORPORATION, Tokyo (JP)

( * ) Notice: Subject to any disclaimer, the term of this patent is extended or adjusted under 35 U.S.C. 154(b) by 43 days.

(21) Appl. No.: 15/833,480

(22) Filed: Dec. 6, 2017

(65) Prior Publication Data
US 2018/0109727 A1 Apr. 19, 2018

Related U.S. Application Data (63) Continuation of application No. PCT/JP2016/066811, filed on Jun. 6, 2016.

(30) Foreign Application Priority Data

Jun. 12, 2015 (JP) ................. 2015-119745

(51) Int. Cl.
H04N 9/78 (2006.01)
H04N 5/232 (2006.01)
(Continued)

(52) U.S. Cl.
CPC ..... *H04N 5/23232* (2013.01); *A61B 1/00009* (2013.01); *H04N 7/183* (2013.01);
(Continued)

(58) Field of Classification Search
CPC ........................................................ G02B 6/06
(Continued)

(56) References Cited

U.S. PATENT DOCUMENTS 6,885,801 B1 * 4/2005 Shankar .................. G06T 5/006
385/116
2001/0052929 A1 12/2001 Abe
2006/0082666 A1 4/2006 Abe et al.

FOREIGN PATENT DOCUMENTS

JP H06-181885 A 7/1994
JP 2001-224017 A 8/2001
(Continued)

OTHER PUBLICATIONS

Aug. 23, 2016 International Search Report issued in International Patent Application No. PCT/JP2016/066811.
(Continued)

*Primary Examiner* — Anand S Rao
(74) *Attorney, Agent, or Firm* — Oliff PLC (57) ABSTRACT A video signal distributor that copies a video signal according to a size of a display region of a device, a video signal magnification/reduction section that magnifies or reduces the copied video signal in accordance with a resolution of the device, a first image size change processor that performs image size increase/decrease processing in such a way that the video signal has a magnification that corresponds to a size of a first display region of the device, and a second image size change processor that performs the image size increase/decrease processing in such a way that the video signal has a magnification that corresponds to a size of a second display region of the device, are included.

7 Claims, 5 Drawing Sheets (51) Int. Cl.
*H04N 7/18* (2006.01)
*H04N 9/76* (2006.01)
*A61B 1/00* (2006.01)
*H04N 21/2343* (2011.01)
*H04N 21/258* (2011.01)
*H04N 21/4402* (2011.01)
*H04N 21/45* (2011.01)
*H04N 21/4545* (2011.01)
*H04N 5/225* (2006.01)

(52) U.S. Cl.
CPC ....... *H04N 9/76* (2013.01); *H04N 21/234345* (2013.01); *H04N 21/234363* (2013.01); *H04N 21/25825* (2013.01); *H04N 21/440245* (2013.01); *H04N 21/440263* (2013.01); *H04N 21/4516* (2013.01); *H04N 21/45455* (2013.01); *A61B 1/00045* (2013.01); *H04N 2005/2255* (2013.01)

(58) Field of Classification Search
USPC ..................................................... 348/65–76
See application file for complete search history.

(56) References Cited

FOREIGN PATENT DOCUMENTS

| | | |
|---|---|---|
| JP | 2003-339634 A | 12/2003 |
| JP | 2005-013409 A | 1/2005 |
| JP | 2006-115963 A | 5/2006 |
| JP | 2010-051372 A | 3/2010 |

OTHER PUBLICATIONS

Jul. 10, 2017 Office Action issued in Patent Application No. 2017-519696.

Jul. 18, 2017 Office Action issued in Patent Application No. 2017-519696.

Aug. 23, 2016 Written Opinion issued in International Patent Application No. PCT/JP2016/066811.

\* cited by examiner

IMAGE PROCESSING APPARATUS

CROSS-REFERENCE TO RELATED APPLICATIONS

This application is a continuation application of PCT Application No. PCT/JP2016/066811, filed on Jun. 6, 2016 and based upon and claiming the benefit of priority from the prior Japanese Patent Application No. 2015-119745, filed on Jun. 12, 2015, the entire contents of which are incorporated herein by reference.

BACKGROUND OF THE INVENTION

Field of the Invention

The present invention relates to an image processing apparatus that performs image processing on an imaging signal obtained by performing imaging using an image sensor.

Description of the Related Art

An image processing system performs various types of image processing on an imaging signal that has been output from an image sensor, and outputs the obtained image signal to an external device such as a monitor or a printer.

As an example, in an electronic endoscope device, when an endoscopic image obtained by performing image processing on an imaging signal that has been output from a scope is displayed on a monitor, a mask region is generally provided without displaying the entirety of the imaging region of an image sensor on the monitor. Only an image of a prescribed region within the imaging region of the image sensor is displayed on the monitor.

With regard to a technology for performing variable magnification processing on an image including the mask region described above, a technology has been disclosed for reducing time required for image processing by using a variable magnification mask signal in which a pixel is indicated by information of 1 bit (for example, Japanese Laid-Open Patent Publication No. 2001-224017).

In addition, a technology has also been disclosed for displaying an image obtained by performing imaging using a scope provided with a color filter so as to be a color image that is always indicated by a single point in the sample color space when the same color is imaged regardless of the type of the color filter (for example, Japanese Laid-Open Patent Publication No. 2006-115963). In this technology, the determination of the size of a region to be masked according to the type of the scope has also been disclosed.

Further, a technology has also been disclosed in which a video processing circuit and a display control circuit are included for each output destination device, an endoscopic video signal is distributed and given to these circuits, and each of the circuits processes the endoscopic video signal (for example, Japanese Laid-Open Patent Publication No. 2005-13409).

SUMMARY OF THE INVENTION

An image processing apparatus in one aspect of the present invention includes: a video signal distributor that copies a video signal according to a size of a display region of an output destination device, the video signal being generated from an imaging signal output from an image sensor; a video signal magnification/reduction section that magnifies or reduces the video signal copied by the video signal distributor in accordance with a resolution of the output destination device; a first image size change processor that receives the video signal output from the video signal magnification/reduction section and performs image size increase/decrease processing on the video signal in such a way that the video signal has a magnification that corresponds to a size of a first display region within the size of the display region of the output destination device; and a second image size change processor that receives the video signal output from the video signal magnification/reduction section and performs the image size increase/decrease processing on the video signal in such a way that the video signal has a magnification that corresponds to a size of a second display region within the size of the display region of the output destination device.

DETAILED DESCRIPTION OF THE PREFERRED EMBODIMENTS

An embodiment of the present invention is described below with reference to the drawings.

Figure 1A:
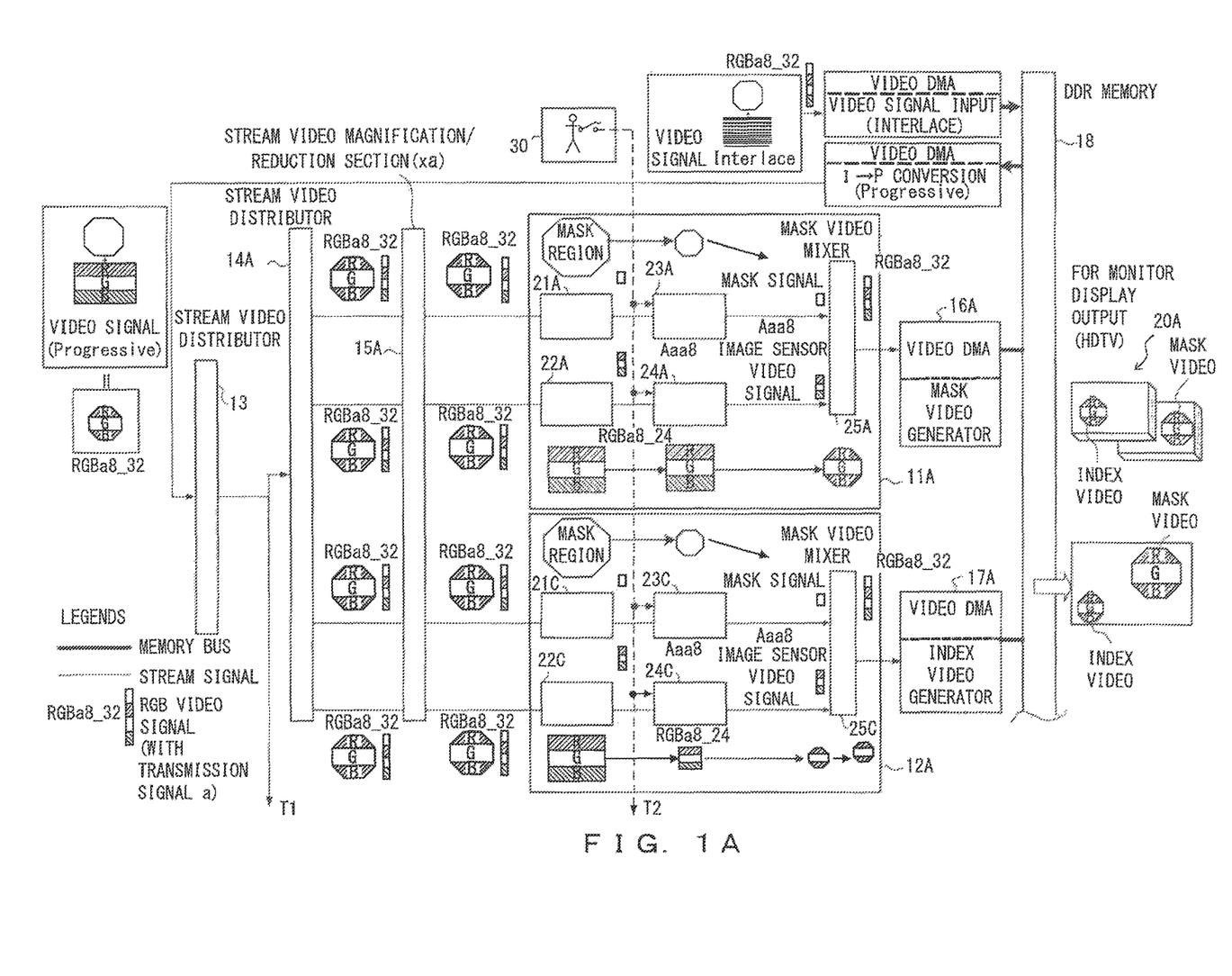
FIG. 1A is a block diagram of an image processing system according to an embodiment.
Figure 1B:
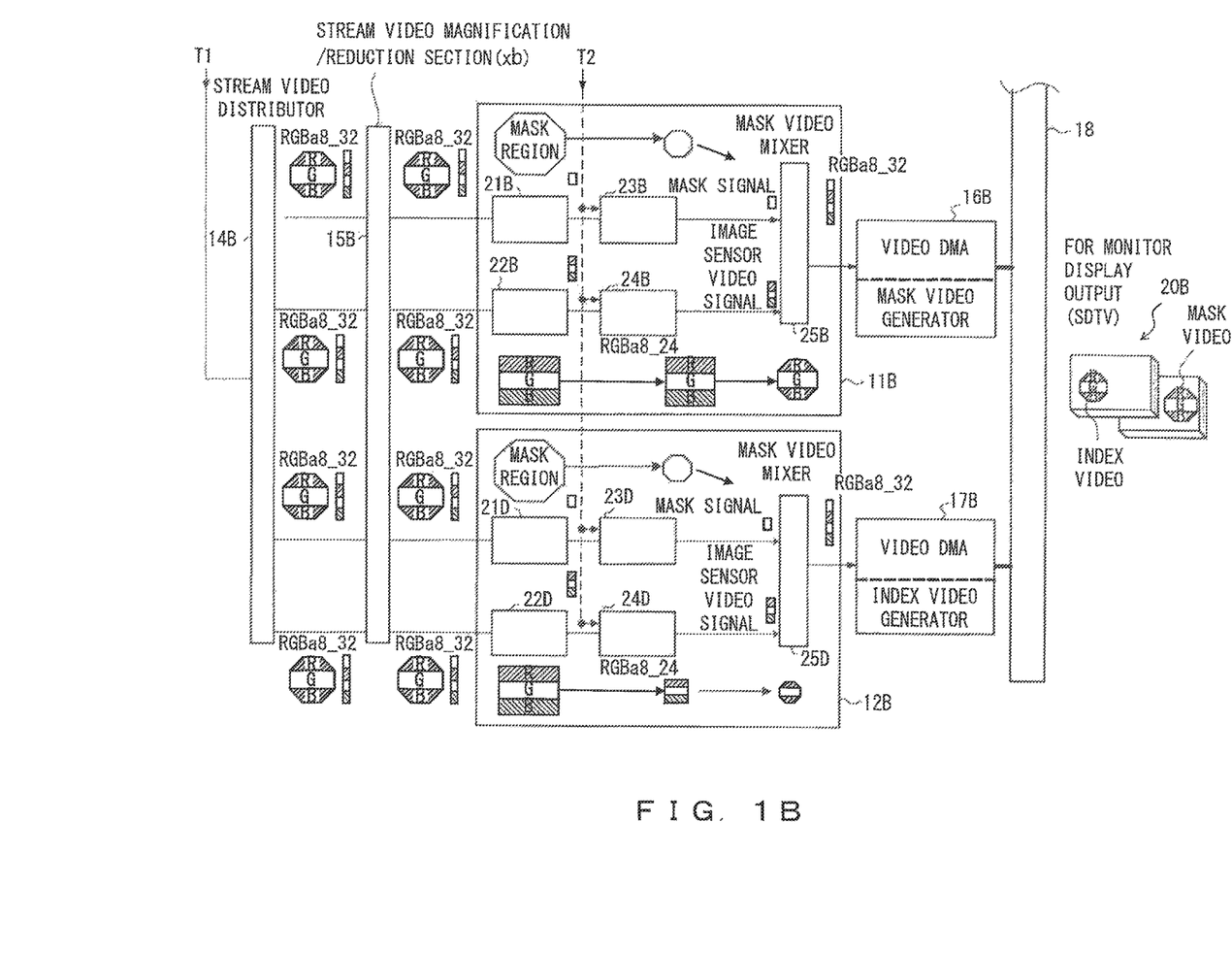
FIG. 1B is a block diagram of an image processing system according to the embodiment.

FIG. 1A and FIG. 1B are block diagrams of an image processing system according to the embodiment. As illustrated in FIG. 1A and FIG. 1B, the image processing system according to the embodiment is applied, for example, to a video processor of an endoscope system. The image processing system is also referred to as an image processing apparatus.

The video processor processes an imaging signal obtained by performing imaging using an image sensor arranged at the distal end of a scope so as to obtain an endoscopic video, and outputs the obtained endoscopic video or image to a plurality of devices such as monitors or printers that are connected via a connector.

The image processing system according to the embodiment is configured to include stream video distributors 13, 14A, and 14B, stream video magnification/reduction sections 15A and 15B, image size change processors 11A, 11B, 12A, and 12B, mask video generators 16A and 16B, index video generators 17A and 17B, and a double-data-rate (DDR) memory 18. The mask video generator is also referred to as a mask generator.

A bit stream video signal (hereinafter referred to as a stream video signal) of an endoscopic video generated from an imaging signal that has been input from a scope and a mask video signal for outputting only a prescribed region within an effective region of an image sensor are input to the image processing system of FIG. 1A and FIG. 1B. The image processing system generates a masked endoscopic video that corresponds to each of a plurality of monitors serving as output destination devices on the basis of the stream video signal of the endoscopic video and the mask video signal that have been input. Hereinafter, the masked endoscopic video is also referred to as a mask video.

First, in the image processing system of FIGS. 1A and 1B, a stream video signal of a progressive format that is obtained by performing interlace/progressive (I/P) conversion on an interlaced video signal obtained by imaging is input together with a mask video signal to the stream video distributor 13.

The stream video distributor 13 distributes the stream video signal of the progressive format and the mask video signal according to the number of output destination devices, and outputs the video signal and the mask video signal that have been distributed. Specifically, the stream video distributor 13 copies the video signal and the mask video signal, and outputs them to a plurality of output destinations.

In the embodiment, the mask video signal is configured by a transmission signal. The transmission signal is transmitted by being superimposed onto the video signal, and when the video signal is displayed on a monitor, whether the transmission signal will be transmitted, namely, whether the transmission signal will be output as a mask video, is set in pixel units. The transmission signal will be described later in detail with reference to the drawings.

In this example, the video signal and the mask video signal that have been output from the stream video distributor 13 are further input to the stream video distributors 14A and 14B.

Each of the stream video distributors 14A and 14B distributes the video signal input from the stream video distributor 13 into two signals, generates a mask video from one of the two distributed video signals, and generates an index video from the other of the two distributed video signals.

Here, the index video is an image that is displayed on a monitor in order to indicate on the monitor that a photographing operation has been performed or to enable a user to confirm a photographed image on the monitor, and the index video is formed by a frame image at the timing of the release operation. The index video is generally output on the monitor so as to have a size smaller than the size of the mask video. The stream video distributors 13, 14A, and 14B are also referred to as video signal distributors.

The video signals and the mask video signals that have been output from the stream video distributors 14A and 14B are respectively input to the stream video magnification/reduction sections 15A and 15B.

The stream video magnification/reduction sections 15A and 15B perform magnification/reduction processing on the video signal and the mask video signal according to a monitor serving as an output destination device. In the example illustrated in FIG. 1A, an output destination monitor is a high-definition television (HDTV), and in the example illustrated in FIG. 1B, the output destination monitor is a standard-definition television (SDTV). The stream video magnification/reduction sections 15A and 15B magnify or reduce the video signal and the mask video signal according to the resolution of the output destination monitor.

For the HDTV, the video signal and the mask video signal that have been output from the stream video magnification/reduction section 15A are input to the image size change processors 11A and 12A. For the SDTV, the video signal and the mask video signal that have been output from the stream video magnification/reduction section 15B are input to the image size change processors 11B and 12B. The stream video magnification/reduction sections 15A and 15B are also referred to as video signal magnification/reduction sections.

When a user inputs an instruction for magnification or reduction via a user operation section 30, the image size change processors 11A, 11B, 12A, and 12B perform image size change processing on the video signal and the mask video signal so as to have the magnifications of a mask video and an index video.

Information relating to a magnification for changing an image size, such as a magnification at the time of increasing an image size or a magnification at the time of reducing an image size, is stored in advance in a storage (not illustrated) such as a non-volatile memory, for each output destination external device.

Each of the image size change processors 11A, 11B, 12A, and 12B reads information relating to a magnification for changing an image size that corresponds to an output destination external device from a memory or the like, and performs image size change processing according to the read information. Details of the image size change processing will be described later.

The video signal and the mask video signal on which the image size change processing has been performed are input to the mask video generator 16A or 16B and the index video generator 17A or 17B. Each of the mask video generators 16A and 16B and the index video generators 17A and 17B includes a video direct memory access (DMA).

Each of the mask video generators 16A and 16B and the index video generators 17A and 17B combines the video signal and the mask video signal that have been input from the image size change processor 11A, 11B, 12A, or 12B, and generates a combined image signal. The generated combined image signal is transferred to each of the video DMAs, and is written to the DDR memory 18.

The DDR memory 18 stores the combined image signals (the index videos+the mask videos) that have been transferred from the mask video generators 16A and 16B and the index video generators 17A and 17B via a memory bus, and outputs the stored combined image signals to monitors via respective interfaces (not illustrated).

As described above, in the image processing system according to the embodiment, when an instruction to magnify or reduce an endoscopic video to be displayed on a monitor is issued via the user operation section 30, processing for changing (increasing or decreasing) an image size is performed in parallel for respective monitors. Namely, in the image processing system according to the embodiment, an image size change processor (in the example of FIG. 1A and FIG. 1B, the image size change processors 11A and 11B) is included for each output destination device, and therefore there is no need to wait until a combined image signal for another monitor is generated. By doing this, combined image signals are output to monitors without delay.

The configurations of the image size change processors 11A and 11B in FIG. 1A and FIG. 1B and a method for changing the image size of a mask video are described next in detail. In the description below, when the image size change processor 11A for the HDTV and the image size change processor 11B for the SDTV do not need to be distinguished from each other, the reference numerals A and B are omitted.

An image size change processor 11 is configured to include a mask signal extractor 21, a video signal extractor 22, a mask magnification/reduction section 23, an observation image magnification/reduction section 24, and a mask video mixer 25. As described above, a stream video signal and a mask video signal that have been magnified or reduced according to the resolution of an output destination monitor by a stream video magnification/reduction section 15 are input to the image size change processor 11.

First, a mask video is described below with reference to the drawings, before the manner in which the image size change processor 11 processes the stream video signal and the mask video signal that have been input so as to magnify or reduce the mask video.

Figure 2:
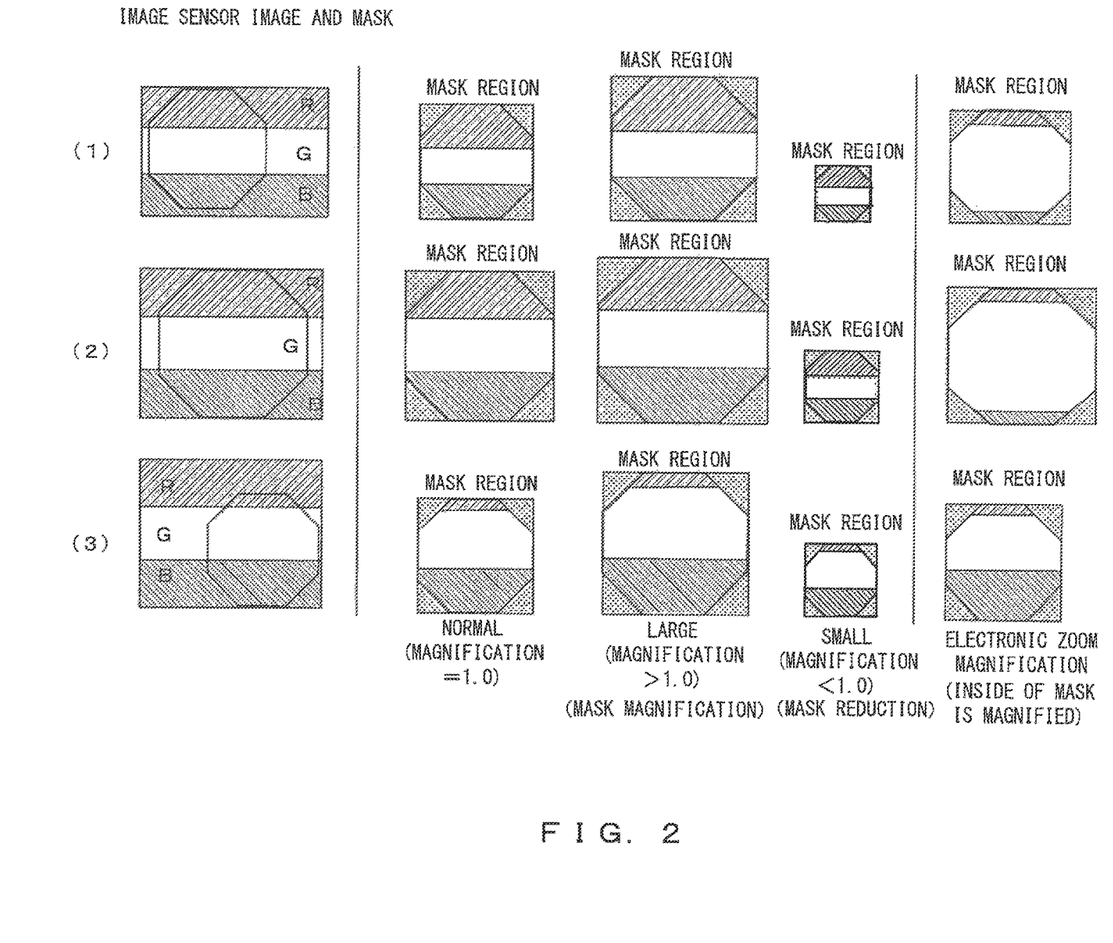
FIG. 2 is a diagram explaining an increase/decrease in the image size of a mask video.

FIG. 2 is a diagram explaining an increase/decrease in the image size of a mask video.

An effective region of an image sensor and a mask region are schematically illustrated in a left-hand column of FIG. 2. In this example, the mask region is octagonal.

A pixel of a region that will be set to be a mask region within the effective region of the image sensor and a portion that will be set to be a mask region change according to the type of the image sensor. In the drawing, the effective region of the image sensor is illustrated by using R (red), G (green) and B (blue) in order to make it visually recognizable that a range and a position that will be set in the mask region change according to the type of the image sensor. In FIG. 2, three cases, (1) to (3), are illustrated.

An endoscope system including the image processing system of FIG. 1A and FIG. 1B stores information relating to a mask region, such as the range, position, or shape of the mask region, according to the type of an image sensor at the distal end of a scope in a storage such as a non-volatile memory that is not illustrated in FIG. 1A and FIG. 1B. The information relating to the mask region according to the type of the image sensor is also referred to as mask image information.

In the endoscope system, information such as the range, position, or shape of a mask region that corresponds to the type of an image sensor to be used is read from a memory or the like, and a mask video signal is generated in association with a stream video signal on the basis of the read information.

Stated another way, a value indicating that pixel data to be used as a mask video within pixel data indicated by a stream video signal will be transmitted is set in a mask video signal in association with the pixel data to be used as the mask video. A value indicating that pixel data that will not be used as a mask video (pixel data outside a mask region) will not be transmitted may be set in the mask video signal in association with the pixel data that will not be used as the mask video.

In the image size change processor 11, the mask signal extractor 21 extracts the mask video signal indicating the mask region from the input signal, and the video signal extractor 22 extracts the stream video signal. The mask signal extractor 21 and the video signal extractor 22 read information relating to the mask region, such as the range, position, or shape of the mask region, from a memory or the like, and respectively determine a video signal included in the mask region and the mask video signal so as to extract the signals. The mask video signal extracted by the mask signal extractor 21 is input to the mask magnification/reduction section 23, and the stream video signal extracted by the video signal extractor 22 is input to the observation image magnification/reduction section 24.

The mask magnification/reduction section 23 performs magnification/reduction processing on a mask according to a set magnification, and the observation image magnification/reduction section 24 performs magnification/reduction processing on an endoscopic image (the stream video signal).

In this example, when an instruction for magnification or reduction is input via the user operation section 30, the mask magnification/reduction section 23 sets a prescribed magnification that exceeds 1.0 or a prescribed magnification that is smaller than 1.0.

In the center column of FIG. 2 (three columns in the center of FIG. 2), images of a normal magnification, magnified images, and reduced images are schematically illustrated in order from the left. When an instruction for magnification or reduction is input, the respective images of the mask region of a normal magnification are magnified or reduced.

In the right-hand column of FIG. 2, images that have been magnified using an electronic zoom are illustrated for the purpose of comparison with images that have been magnified or reduced according to an operation of the user operation section 30. In this case, only images within the mask regions are magnified without changing the sizes of the mask regions.

The manner in which, when a video signal and a mask video signal on a single line of a screen are input to the observation image magnification/reduction section 24 and the mask magnification/reduction section 23, a stream video signal and the mask video signal are changed in magnification/reduction processing performed on an image is described below with reference to FIG. 3.

Figure 3:
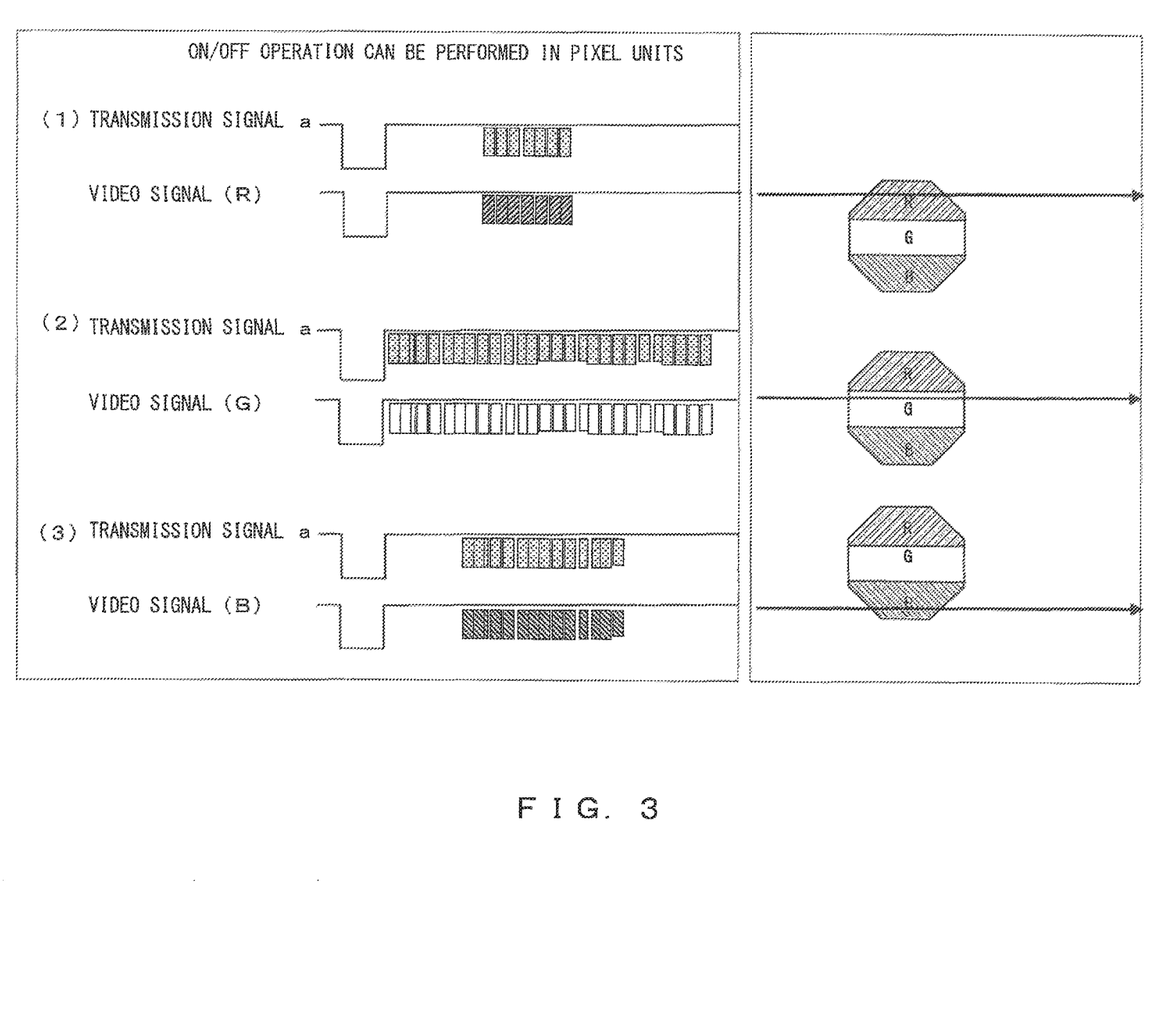
FIG. 3 schematically illustrates a video signal and a mask video signal.

FIG. 3 schematically illustrates a stream video signal (hereinafter abbreviated as a video signal) and a mask video signal (hereinafter abbreviated as a transmission signal). In FIG. 3, the three cases (1) to (3) of the manner in which a video signal and a mask video signal on a certain line are changed in magnification/reduction processing are illustrated.

(1) indicates a video signal and a mask video signal (transmission signal a) after reduction processing, (2) indicates a video signal and a mask video signal (transmission signal a) after magnification processing, and (3) indicates a video signal and a mask video signal (transmission signal a) of a normal magnification in a case in which magnification/reduction processing is not performed. In images of all of the magnifications, transmission signal a is set in the state "transmission (ON)" in association with a video signal that configures a mask video.

As schematically illustrated in FIG. 3, the observation image magnification/reduction section 24 changes (increases or reduces) the number of pixels on a line according to a prescribed magnification that has been set due to an operation of the user operation section 30. In addition, the mask magnification/reduction section 23 increases or reduces a transmission signal on the line at a ratio that is similar to a ratio at which the number of pixels of the video signal is increased or reduced. Taking the observation image magnification/reduction section 24A and the mask magnification/reduction section 23A of FIG. 1A as an example, when the observation image magnification/reduction section 24A changes the number of pixels of the mask video to c times, the mask magnification/reduction section 23A also changes the number of pixels of transmission signal a to c times. The video signal and the mask video signal (transmission signal a) on which magnification/reduction processing has been performed by the observation image magnification/reduction section 24A and the mask magnification/reduction section 23A are input to the mask video mixer 25A.

The mask video mixer 25 synchronizes the signals input from the observation image magnification/reduction section 24 and the mask magnification/reduction section 23, and outputs the signals to a mask video generator 16. The mask video mixer 25 is also referred to as an image signal combiner.

The mask video generator 16 generates a mask video 20 from the video signal and the transmission signal by alpha blending. Specifically, the mask video generator 16 determines that pixels in which a value indicating "transmission" has been set in a corresponding transmission signal a within a video signal are pixels that will configure a mask video, and the mask video generator 16 transmits the pixels. The mask video generator 16 does not transmit the other pixels. By doing this, the mask video generator 16 generates the mask video 20.

As described above, the generated mask video 20 is written to the DDR memory 18 by DMA transfer, and a signal of the mask video is output from the DDR memory 18 to an output destination device.

In the image size change processor 11, the observation image magnification/reduction section 24 and the mask magnification/reduction section 23 perform magnification/reduction processing at the same magnification. By doing this, when generating a magnified or reduced mask video, the mask video generator 16 only determines which portion of a video signal will configure a mask video in accordance with a transmission signal. Accordingly, processing for generating a magnified or reduced mask video can be performed at high speed.

Further, in the image processing system of FIG. 1A and FIG. 1B, an index video for indicating on a monitor that a release operation has been performed can be magnified or reduced according to an operation of the user operation section 30 similarly to the mask video.

Comparing with the mask video, the index video has a position in which the index video is arranged within an image of a signal frame, the size of the index video, and a magnification/reduction ratio that are different from those of the mask video. However, a method for changing an image size of the index video is similar to a method in which the image size change processors 11A and 11B change the image size of the mask video. Stated another way, the configurations of the image size change processors 12A and 12B that change the image size of the index video, such as the mask signal extractor 21, the video signal extractor 22, or the mask magnification/reduction section 23, are similar to the configurations of the image size change processors 11A and 11B that change the image size of the mask video, and the description thereof are given by using similar reference numerals.

The image size change processor 11A and/or 12A is also referred to as a first image size change processor, and the image size change processor 11B and/or 12B is also referred to as a second image size change processor.

In addition, assume, for example, that the magnification of an image size after changing by the stream video magnification/reduction section 15A is a times. Similarly, assume that the magnification of an image size of the stream video magnification/reduction section 15B is b times. Assume that the magnification of an image size of the mask magnification/reduction section 23A and the observation magnification/reduction section 24A is c times, and that the magnification of an image size of the mask magnification/reduction section 23C and the observation magnification/reduction section 24C is d times. Further, assume that the magnification of an image size of the mask magnification/reduction section 23B and the observation magnification/reduction section 24B is e time, and that the magnification of the mask magnification/reduction section 23D and the observation magnification/reduction section 24D is f times.

As described above, in the image processing system of FIG. 1A and FIG. 1B, the image size change processor 11 magnifies or reduces a mask video by using transmission signal a. By using transmission signal a, a troublesome process such as a process for performing magnification/reduction processing on each of an original image and a mask before magnification/reduction is not required, and a mask video can be simply magnified or reduced.

In addition, in the image processing system according to the embodiment, a stream video signal can be sequentially processed from the head and can be output in contrast to a method for performing magnification/reduction processing on each of an original image and a mask, and a pixel that has been processed can be sequentially displayed on a monitor without waiting until image data of a single frame is generated.

Figure 4:
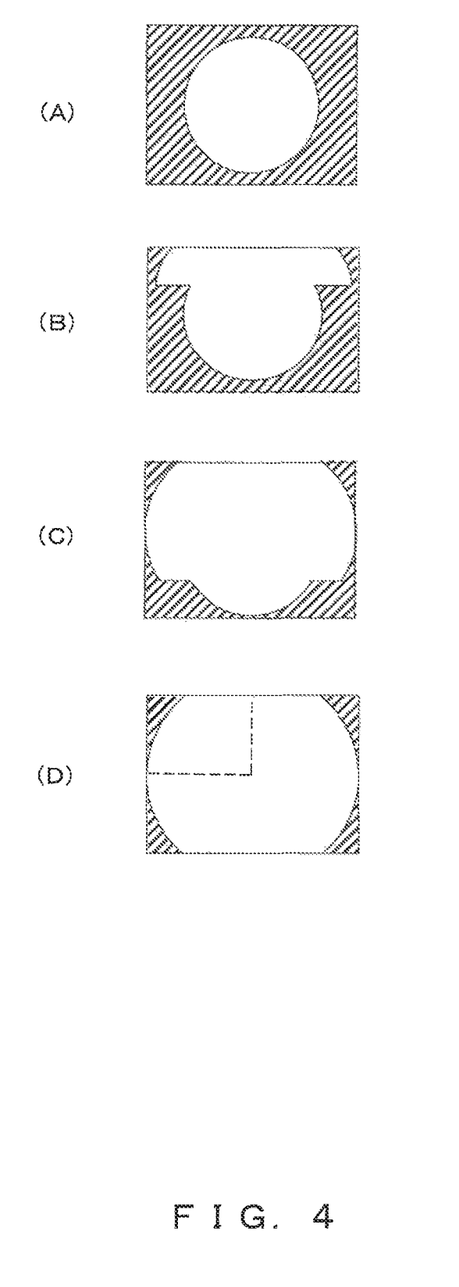
FIG. 4 illustrates an overview of a conventional method for changing an image size.

FIG. 4 illustrates an overview of a conventional method for changing an image size described in Japanese Laid-Open Patent Publication No. 2001-224017 described above. (A) to (D) of FIG. 4 indicate states in respective stages of processing for changing the magnification of a mask video. As illustrated in FIG. 4, in a conventional method for changing an image size, an image cannot be displayed on a monitor in stages (B) and (C) in which an image is being processed, and it is necessary to wait until stage (D) is reached. Namely, in the conventional method for changing an image size, in order to connect an image processing system to a plurality of monitors and to make each of the plurality of monitors display an image, image processing for each of the plurality of monitors needs to be performed sequentially.

In contrast, in the image processing system according to the embodiment, image signals can be output to a plurality of external devices without increasing a delay.

Note that the present invention is not limited exactly to the above embodiments, and can be embodied in the implementation phases by modifying constitutional elements without departing from the spirit of the present invention. Also, it is possible to form various inventions by an appropriate combination of a plurality of constituent elements disclosed in the above embodiments. For example, all the constituent elements disclosed in the above embodiments may be combined appropriately. Further, constituent elements selected from different embodiments may be combined appropriately. It is as a matter of course that these various modifications and applications are possible without departing from the spirit of the present invention.

EXPLANATIONS OF LETTERS OR NUMERALS 11A, 11B, 12A, and 12B Image size change processors
13, 14A, and 14B Stream video distributors
21A to 21D Mask signal extractors
22A to 22D Video signal extractors
23A to 23D Mask magnification/reduction sections
24A to 24D Observation image magnification/reduction sections
25A to 25D Mask video mixers

What is claimed is:
1. An image processing apparatus comprising:
a processor programmed to function as:
   a video signal distributor that copies a video signal according to a size of a display region of an output destination device, the video signal being generated from an imaging signal output from an image sensor;
   a video signal magnification/reduction section that magnifies or reduces the video signal copied by the video signal distributor in accordance with a resolution of the output destination device;
   a first image size change processor that receives the video signal output from the video signal magnification/reduction section and performs a first image size increase/decrease processing on the video signal to change a data size of the video signal, such that a video of the video signal has a magnification that corresponds to a size of a first display region within the size of the display region of the output destination device; and a second image size change processor that receives the mask video signal output from the video signal magnification/reduction section and performs a second image size increase/decrease processing on the mask video signal to change a data size of the video signal, such that a video of the video signal has a magnification that corresponds to a size of a second display region within the size of the display region of the output destination device, the first image size increase/decrease processing and the second image size increase/decrease processing being performed simultaneously, wherein:

the mask signal indicates a mask region, which is a portion of the video that corresponds to an effective region of the image sensor based on parameters of the image sensor, the increase/decrease processing removing pixel data from the video signal that is not included in the mask region, and a mask video generator generates a mask video by combining the processed mask signal, which has undergone increase/decrease processing, and the video signal.

2. The image processing apparatus according to claim 1, wherein each of the first image size change processor and the second image size change processor includes:

a mask signal extractor that extracts a mask video signal that corresponds to a non-display region from each of a first video signal that has been distributed for the size of the first display region by the video signal distributor and a second video signal that has been distributed for the size of the second display region by the video signal distributor;

a video signal extractor that extracts a video signal that corresponds to a display region from each of the first video signal and the second video signal that have been distributed from the signal distributor; and an image signal combiner that combines the mask video signal and the video signal that corresponds to the display region that have been output from the first image size change processor and the second image size change processor so as to generate a combined image signal, and that outputs the combined image signal to the output destination device.

3. The image processing apparatus according to claim 2, wherein the mask signal extractor and the video signal extractor extract signals in such a way that the mask video signal and the video signal that corresponds to the display region have an identical magnification, and outputs the mask video signal and the video signal that corresponds to the display region that have been extracted to the image signal combiner.

4. The image processing apparatus according to claim 3, further comprising:

a mask video generator that sets in pixel units whether the video signal that corresponds to the display region will be transmitted when the video signal that corresponds to the display region is output to an external device, in accordance with a transmission signal that has been superimposed onto the video signal that corresponds to the display region as the mask video signal.

5. The image processing apparatus according to claim 1, further comprising:

a storage that stores information relating to a size change magnification according to the output destination device, wherein the first image size change processor and the second image size change processor perform the image size increase/decrease processing in accordance with the information relating to the size change magnification stored in the storage.

6. The image processing apparatus according to claim 5, wherein the storage further stores mask image information according to types of a plurality of image sensors, and the first image size change processor and the second image size change processor perform the image size increase/decrease processing on each of the mask video signal and the video signal that corresponds to the display region in accordance with the mask image information stored in the storage.

7. The image processing apparatus according to claim 1, wherein the image processing apparatus is an image processing apparatus provided in a processor for an endoscope.

* * * * *